(12) United States Patent
Kale et al.

(10) Patent No.: US 10,722,389 B2
(45) Date of Patent: Jul. 28, 2020

(54) ENDOLUMINAL STENT

(71) Applicant: SAHAJANAND MEDICAL TECHNOLOGIES PRIVATE LIMITED, Gujarat (IN)

(72) Inventors: Sunil Pundlikrao Kale, Gujarat (IN); Bhautikkumar Chandulal Khanpara, Gujarat (IN)

(73) Assignee: SAHAJANAND MEDICAL TECHNOLOGIES PRIVATE LIMITED, Surat (IN)

( * ) Notice: Subject to any disclaimer, the term of this patent is extended or adjusted under 35 U.S.C. 154(b) by 139 days.

(21) Appl. No.: 15/542,072

(22) PCT Filed: Jan. 6, 2016

(86) PCT No.: PCT/IN2016/050005
§ 371 (c)(1),
(2) Date: Jul. 6, 2017

(87) PCT Pub. No.: WO2016/110875
PCT Pub. Date: Jul. 14, 2016

(65) Prior Publication Data
US 2018/0000618 A1    Jan. 4, 2018

(30) Foreign Application Priority Data
Jan. 7, 2015 (IN) .............................. 65/MUM/2015

(51) Int. Cl.
*A61F 2/82* (2013.01)
*A61F 2/915* (2013.01)

(52) U.S. Cl.
CPC .... *A61F 2/915* (2013.01); *A61F 2002/91533* (2013.01); *A61F 2002/91583* (2013.01)

(58) Field of Classification Search
CPC ........................................................ A61F 2/82
See application file for complete search history.

(56) References Cited

U.S. PATENT DOCUMENTS

| | | |
|---|---|---|
| 2003/0055485 A1 | 3/2003 | Lee et al. |
| 2004/0133271 A1 | 7/2004 | Jang |
| 2004/0138737 A1 | 7/2004 | Davidson et al. |
| 2004/0267353 A1 | 12/2004 | Gregorich |

FOREIGN PATENT DOCUMENTS

| | | |
|---|---|---|
| DE | 19753123 A1 | 5/1999 |
| EP | 1095632 A2 | 2/2001 |
| EP | 1184007 A2 | 3/2002 |
| EP | 1981433 | 9/2007 |
| WO | WO00/62710 A1 | 10/2000 |
| WO | WO02/26164 A2 | 2/2002 |
| WO | WO2004/084764 A2 | 10/2004 |
| WO | WO2006/005026 A2 | 1/2006 |
| WO | WO2008/008291 A2 | 1/2008 |
| WO | WO2009/012417 A1 | 1/2009 |

*Primary Examiner* — Matthew W Schall
(74) *Attorney, Agent, or Firm* — Nixon & Vanderhye P.C.

(57) ABSTRACT

An endoluminal stent (100) is described herein. In an embodiment, the endoluminal stent (100) includes a plurality of sinusoidal-shaped expandable ringlets (102) provided in parallel to form a tubular structure of the endoluminal stent (100). Further, adjacent ringlets (102) can be connected to each other by one or more asymmetrical offset connectors (108), the offset connectors (108) being non-linear in structure.

7 Claims, 3 Drawing Sheets

ENDOLUMINAL STENT

CROSS-REFERENCE TO RELATED APPLICATIONS

This application is a national stage application of international patent application No. PCT/IN2016/050005, filed Jan. 6, 2016 and entitled "Endoluminal Stent," which claims the benefit of Indian Patent Application No. 65/MUM/2015 filed on Jan. 7, 2015, and entitled "Endoluminal Stent," both of which are expressly and fully incorporated herein by reference in their entirety.

TECHNICAL FIELD

The present subject matter relates, in general, to medical devices and, particularly but not exclusively, to endoluminal stents.

BACKGROUND

Endoluminal stents are generally tubular-shaped devices fabricated from implantable biocompatible materials and can function to hold open a segment of a blood vessel or other anatomical lumen. Accordingly, such stents can generally be adapted to be implanted into a patient's body lumen, such as blood vessel, to maintain the patency of the lumen. For example, the endoluminal stents can be useful in the treatment of atherosclerotic stenosis in blood vessels.

Conventionally, the endoluminal stents are formed as various structures. For example, the stent can be formed as coiled stainless steel spring; helical wound spring coil; or as a mesh having a zig-zag patterned mesh; a diamond shaped mesh, or a rectangular shaped mesh, or can be formed as other mesh or non-mesh designs.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
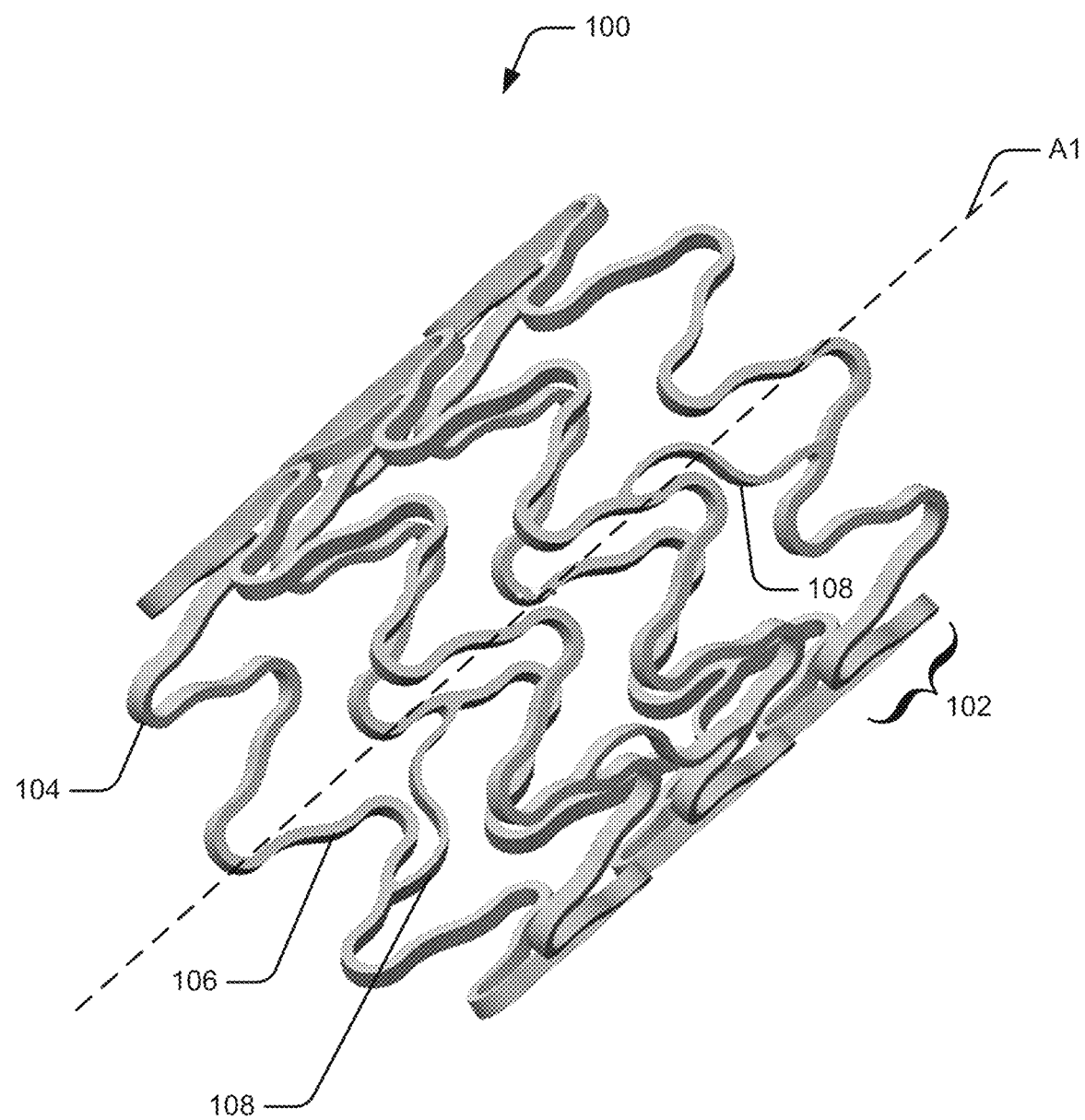
FIG. 1 illustrates a prospective view of an endoluminal stent, in accordance with an embodiment of the present subject matter.

The present subject matter relates to an endoluminal stent, in accordance with an aspect of the present subject matter.

Conventionally, endoluminal stents can be formed in mesh or non-mesh designs, for example, as coiled stainless steel spring; helical wound spring coil; or as a mesh having a zig-zag patterned mesh; a diamond shaped mesh, or a rectangular shaped mesh. Generally, designs of endoluminal stent are aimed at achieving an optimum balance among various functional, performances, and design attributes of the endoluminal stent. Such attributes can include radial crush resistance, crimped profile, radial recoil after crimping, radial recoil after expansion, flexibility along the longitudinal axis in crimped as well as expanded state, foreshortening, longitudinal compression resistance in crimped as well as expanded state, flaring of crowns, corrosion behaviour, radiopacity, strut thickness, fatigue resistance, and side branch access.

Usually, few of these attributes are antagonistic in nature, i.e., improving on one attribute leads to compromise on the other. For example, in few cases, endoluminal stent are designed so as to compromise on longitudinal compression resistance for better flexibility, while in certain other cases, the endoluminal stent designs compromise on crimped diameter for ability to expand at a higher diameter. Still other endoluminal stent designs may compromise on radial crush resistance for lower strut thickness.

In addition, a flexible conventional endoluminal stent can exhibit significant foreshortening when expanded to large diameters, such as cases where expansion diameter of the endoluminal stent is greater than about 4 millimetre (mm). Generally such foreshortening is experienced due to the longitudinal compressive force imparted by expansion of a balloon of a catheter during delivery and deployment of the endoluminal stent in the body lumen.

Further, conventional endoluminal stents may use support structures, say supports in the mesh structure, to enhance length of the endoluminal stent after expansion of the stent. Additionally, providing such support structures may provide flexibility and strength to the endoluminal stent. However, the endoluminal stent having such a structure may exhibit low resistance to axially applied compressive force and, hence, may be prone to axial distortion, say in expanded configuration.

The present subject matter relates to endoluminal stents, in accordance with an aspect of the present subject matter. The endoluminal stents can include but are not limited to balloon expandable stents, self expandable stents, stent grafts and grafts.

According to an embodiment, the endoluminal stent of the present subject matter includes a plurality of sinusoidal-shaped expandable ringlets that may form a lateral surface of the endoluminal stent. Further, the ringlets may be provided coaxially along a central longitudinal axis to form a tubular structure of the endoluminal stent. The sinusoidal-shape can provide for uniform stress distribution across a circumference of the ringlets. In said embodiment, the adjacent ringlets can be connected to each other by one or more asymmetrical offset connectors. Further, the offset connectors can be non-linear in structure. The provision of such connectors in the endoluminal stent provides for high flexibility as well as pushability of the stent during deployment. In addition, such structure of the connectors substantially prevents concentration of stresses at a junction of the connectors with the sinusoidal-shaped expandable ringlets, thereby, minimizing risk of fatigue fracture of the connectors.

In addition, a distance between two adjacent crowns or two adjacent troughs of each sinusoidal-shaped expandable ringlet can be substantially small. Such a design of the endoluminal stent provides better conformability in curvatures of tortuous lumen. Further, two adjacent sinusoidal-shaped expandable ringlets are separated by a substantially small gap. Such a construction of the endoluminal stent provides better conformability for the stent even in curvatures of tortuous lumen. Additionally, such structure can provide for optimal support or scaffolding during deployment and in the deployed condition of the endoluminal stent.

The present subject matter can be used in variety of applications. For example, the endoluminal stent, in accordance with the present subject matter, can be used in peripheral applications where expansion diameter of the endoluminal stent is greater than about 4 mm. Further, such a stent can withstand longitudinal compression force applied by proximal and distal ends of a balloon during expansion, when used for deployment. This is possible owing to the nonlinear, asymmetric interlink design of the endoluminal stent. Such a design can resist longitudinal compression but can also elongate itself in length when stretched longitudinally by the expanding balloon. As a result the stent exhibits positive foreshortening and the length of the endoluminal stent can increases when expanded to a larger diameter.

Additionally, the endoluminal stent is highly flexible and demonstrates very good deliverability and conformability after deployment with high longitudinal compression resistance in crimped as well as in expanded state. As a result of the high longitudinal compression resistance, the endoluminal stent can also exhibit high degree of pushability, i.e., a measure of the ease with which the endoluminal stent can be pushed in the body lumen. The stent exhibits uniform stress distribution due to the non-linear design of the sinusoidal-shaped expandable ringlets. In addition, the asymmetrical connectors prevent stress concentration at the junction of the connector with the ringlets. Conventionally, the offset connectors lead to significant twisting of adjacent ringlets with respect to each other due to generation of unbalanced forces across the two ends of the connector during stent expansion. However, the present subject matter provides minimal twisting in adjacent ringlets with respect to each other due to minimization of unbalanced forces across the connector. The connector is longer in length compared to conventional offset connectors. The longer length and the sinusoidal shape of the connector enables the connector to deform without creating significant unbalanced forces across the two ends of the connector, thus minimizing the twisting of ringlets with respect to each other.

These and other advantages of the present subject matter would be described in greater detail in conjunction with the following figures. While aspects of the endoluminal stents can be implemented in any number of different configurations, the embodiments are described in the context of the following description.

FIG. 1 illustrates a prospective view of an endoluminal stent 100 which includes a plurality of ringlets 102 that may be provided coaxially along a central longitudinal axis A1 form a tubular or cylindrical structure of the endoluminal stent 100. In an example, the ringlets 102 may form a lateral surface of the endoluminal stent 100. Further, each of the ringlet 102 may have a sinusoidal structure along a length of the ringlet 102. In one example, the plurality of ringlets 102 can be interconnected in series in a pattern. The endoluminal stent 100 is in general cylindrical in shape and is designed to be able to shrink circumferentially to a small diameter for ease of delivery and can be expanded radially to a greater diameter for deployment.

According to an aspect, the ringlets 102 are a collection of curved parts referred to as crowns 104, connected by connecting elements 106 along its circumference. In an example, the connecting elements 106 can be straight or wavy. Further, the constructional and operational details of the ringlets 104 may be explained in details with respect to FIG. 2.

Further, in an example, the adjacent ringlets 102 can be interconnected though one or more connectors 108. The connectors 108 can be straight or non-linear, say sinusoidal, or a combination thereof. The connectors 108, in operation, may resist foreshortening of the endoluminal stent 100, that otherwise would have caused by compressive force induced in the endoluminal stent 100 during deployment. The manner by which the connector 108 connects the adjacent ringlets 104 and how the connectors 108 resist foreshortening of the endoluminal stent 100 would be explained in details with respect to FIG. 3.

The endoluminal stent 100 can be made up of a metal, metal alloy, a biodegradable polymer, a combination of biodegradable polymer, a biostable polymer or a combination of biostable polymers, a combination of biodegradable and biostable polymers, a combination of metal or metal alloy along with a biodegradable polymer or a combination of biodegradable polymers, a combination of a metal or metal alloy along with a biostable polymer or combination of biostable polymers. In addition the endoluminal stent 100 can be coated with a therapeutic agent in combination of a biodegradable polymer coating, a biostable polymer coating, a combination of biostable and biodegradable polymer coating, a combination of biodegradable and biostable coating. The endoluminal stent 100 can also be coated with a passive coating or a combination of passive coating and a biodegradable coating containing a therapeutic agent. Alternatively, the endoluminal stent 100 can be coated with nanoparticles of the therapeutic agent with or without a passive coating. For instance, the endoluminal stent 100 can be used as a drug eluting stent in combination with therapeutic agents.

The endoluminal stent 100 can be formed from materials that can be deformed plastically to allow crimping and expansion of the endoluminal stent 100. Representative examples of metals and metal alloys that can be used to fabricate the device described in present subject matter include but are not limited to Stainless steel, Tantalum, Niobium, Magnesium alloys, Zinc alloys, L605, MP25N, and Nitinol.

Representative examples of polymers that can be used to fabricate the device described in present subject matter include but are not limited to polymers of L-lactide, Glycolide or combinations of thereof, poly(hydroxybutyrate), polyorthoesters, polyanhydrides, poly(glycolic acid), poly(glycolide), poly(L-lactic acid), poly(L-lactide), poly(D-lactic acid), poly(D-lactide), poly(caprolactone), poly(trimethylene carbonate), polyester amide, polyesters, polyolefins, polycarbonates, polyoxymethylenes, polyimides, polyethers, and copolymers and combinations thereof.

Figure 2:
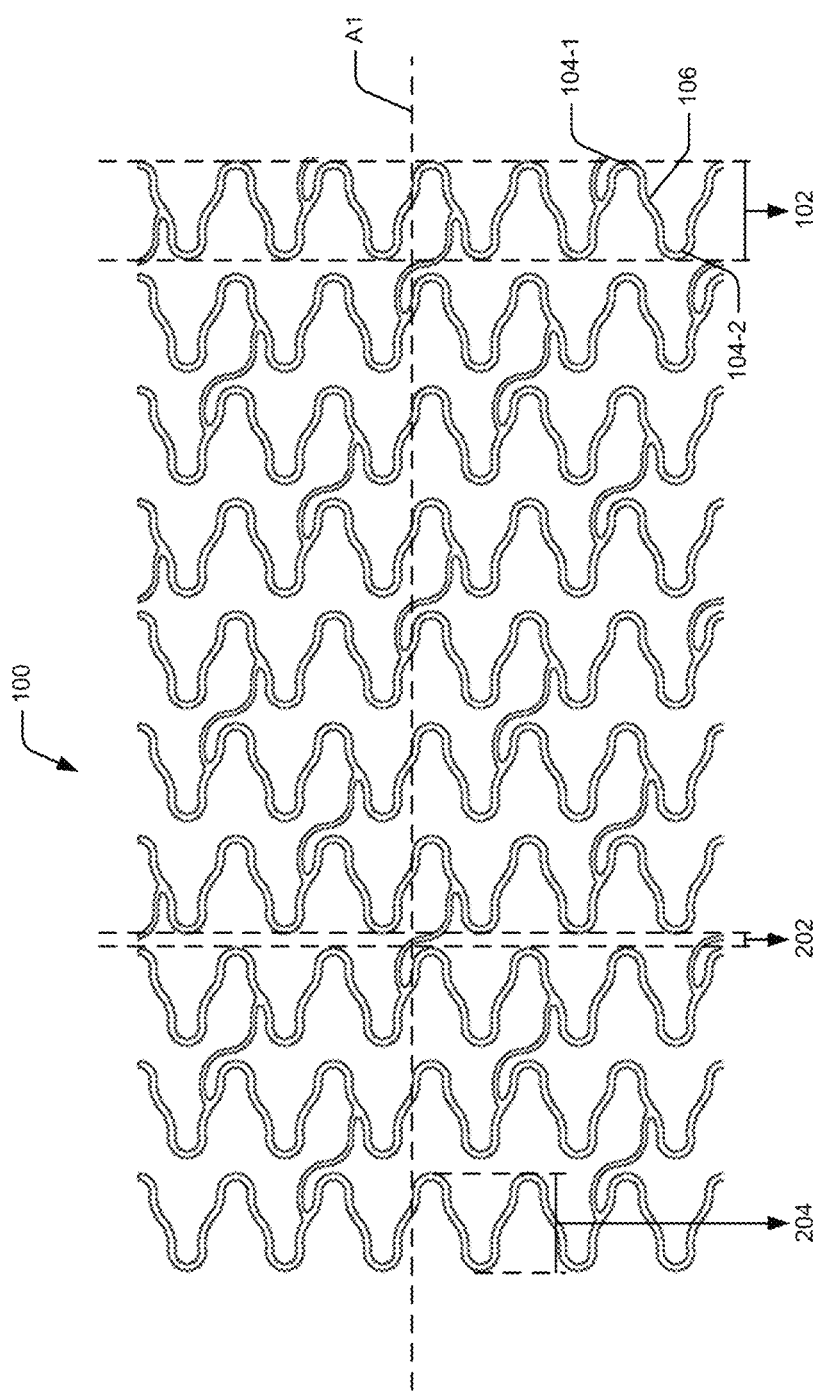
FIG. 2 illustrates the endoluminal stent viewed in a planar state, in accordance with an embodiment of the present subject matter.

FIG. 2 illustrates the endoluminal stent 100 in planar view. The ringlets 102 can include non-linear structures, say sinusoidal-shaped structures, for uniform stress distribution and preventing deformation during crimping and deployment. In an example, the ringlet 102 may have a plurality of arc-shaped first crowns 104-1 and a plurality of arc-shaped second crowns 104-2; collectively referred to as crowns 104 (shown in FIG. 1). In one example, the first crowns 104-1 and the second crowns 104-2 may have curved sections. Further, each of the first crowns 104-1 and second crowns 104-2 may have a first end and a second end. In an example, the first crowns 104-1 and the second crowns 104-2 may be placed such that an orientation of the first crowns 104-1 may be opposite to an orientation of the second crown 104-2. In one example, inner surfaces of the curved sections of the first crown 104-1 and the second crown 104-2 may face towards each other. As mentioned previously, the crowns 104 are connected with each other by one or more connecting elements 106. In one example, the connecting element 106 may connect a first end of the one first crown 104-1 to a second end of the opposite facing second crown 104-2 so that the sinusoidal structure may be formed.

In case the ringlets 102 are formed as having sinusoidal shape, the ringlets 102 can be in phase with respect to each other for providing uniform scaffolding or support with gaps 202 in the axial direction between adjacent ringlets 102. Such a provision can minimize risk of protrusion of plaque into the lumen in cases where the endoluminal stent 100. The ringlet 102 can have a predefined distance 204 between the two adjacent crowns 104 or two adjacent troughs of the sinusoidal-shape.

Generally, the endoluminal stent 100 may be deployed in the endovascular lumen by a balloon catheter. Further, in order to fix the endoluminal stent 100 in the inner walls of the endovascular lumen, the balloon catheter may alternatively inflated and deflated. During such operation, the endoluminal stent 100 may be subject to fatigue loading. This further increase the chances of structural failure of the endoluminal stent 100. However, the sinusoidal structure of the may prevent any stress concentration across a length of the endoluminal stent 100 thereby avoiding structural failure of the endoluminal stent 100.

In an example, the endoluminal stent can have the dimensions as provided in Table 1 below:

TABLE 1

| Design Elements | Dimension in millimeters (lower limit of the range) | Dimension in millimeters (higher limit of the range) |
| --- | --- | --- |
| Distance 204 between two adjacent crowns 104 of ringlet 102 | 0.7 | 2.0 |
| Radius of crown 104 | 0.200 | 0.300 |
| Radius of sinusoidal structure 310 | 0.400 | 0.700 |
| Radius of connectors 108 when they are sinusoidal in shape | 0.250 | 0.7500 |
| Gap 202 between adjacent ringlets 102 | 0.100 | 0.500 |
| Radius of curved portions 302, 304 of the connector 108 | 0.35 | 0.75 |
| Radius of curved portions 306, 308 of ringlet 102 | 0.21 | 0.71 |
| Strut thickness | 0.040 | 0.200 |
| Strut width | 0.040 | 0.200 |

Figure 3:
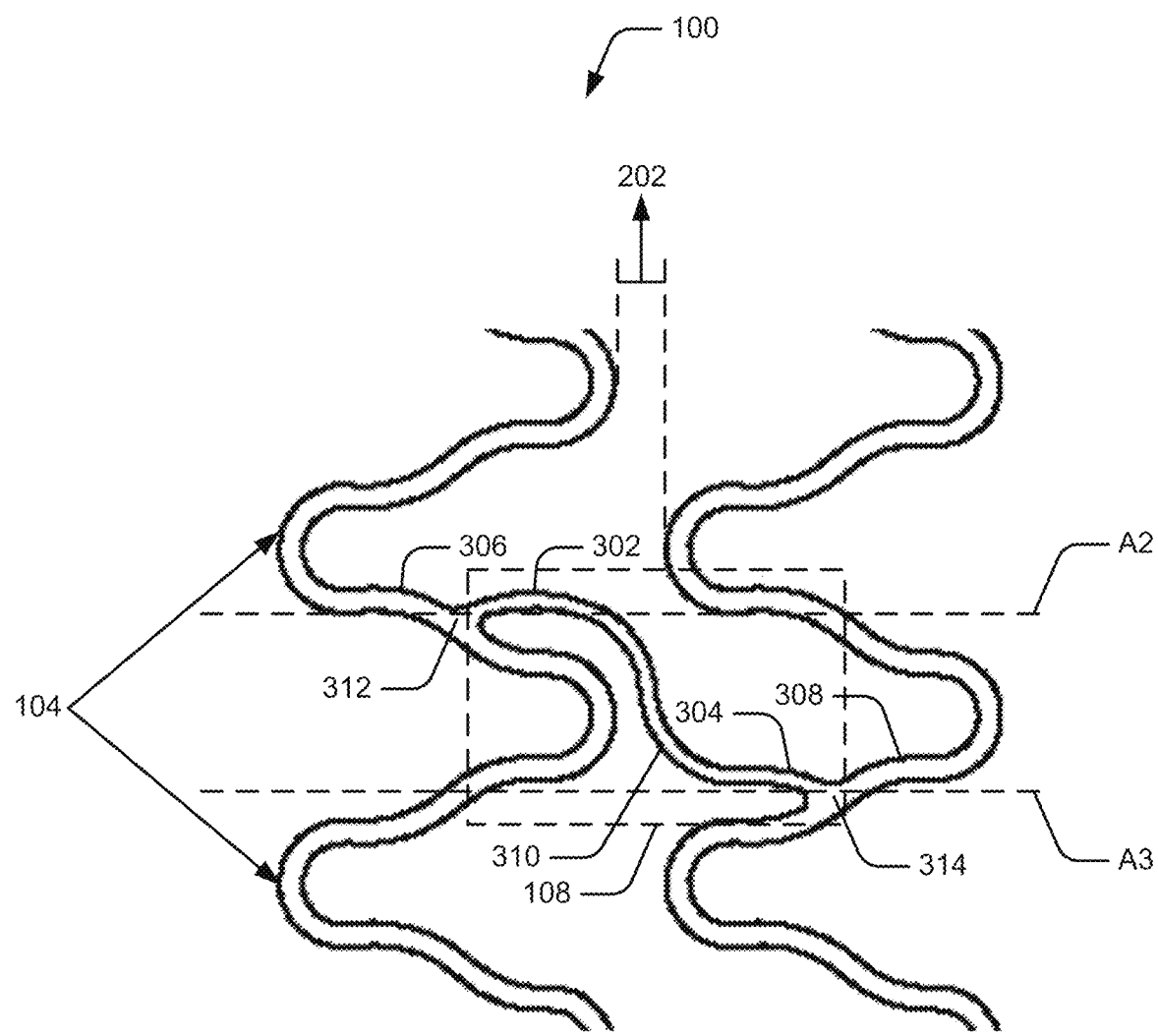
FIG. 3 illustrates a magnified view of the endoluminal stent, in accordance with an embodiment of the present subject matter.

FIG. 3 illustrates a magnified view of the endoluminal stent 100 showing design of the connectors 108. In an example, the connector 108 can connect the mid portions of the connecting elements 106 of the adjacent ringlets 102. In another example, the connector 108 can connect the crown 104 of one the ringlet 102 to the crown 104 of the adjacent ringlet 102. The connector 108 can be asymmetric in design and can have a non-linear structure. In such a case, both the ends of the connector 108 can have curved portions 302 and 304 in the opposite direction of the curved portions 306 and 308 of the ringlet 102 at the junction 308 with the connector 108. In the example shown in FIG. 3, the curved portions 302 and 304 of the connector 108 can be connected together through a sinusoidal structure 310. In another example, the curved portions 302 and 304 of the connector 108 can be connected together through a straight structural element, or a combination of straight and sinusoidal structures.

In one implementation, one end of the curved portion 302 of the connector 108 may be coupled to the curved portion 306 of the adjacent ringlet 102 at a first junction 312. In addition, another end of the curved portion 304 of the connector 108 may be coupled to the curved portion 308 of the adjacent ringlet 102 at a second junction 314. In the illustrated implementation, an axis A2 parallel to the central longitudinal axis A1 and passing through the first junction 312 may be at an offset to another axis A3 parallel to the central longitudinal axis A1 and passing through the second junction 314. Accordingly, one end of the connector 108 may be coupled to one ringlet 102 at the first junction 308 and another end of the connector 108 may be coupled to the adjacent ringlet 102 at the second junction 310, such that the axis A2 passing through the first junction 308 and parallel to the central longitudinal axis A1 is at an offset with respect to another axis A3 passing through the second junction 310 and parallel to the central longitudinal axis A1.

In an example, the connectors 108 can be equal in number to the number of crowns 104 in the ringlet 102, whereas in another example, the connectors 108 can be less than the number of crowns 104 in the ringlet 102. The connectors 108 can be arranged cyclically or at 90 degree offset along the longitudinal axis of the endoluminal stent 100.

The operation of the deployment of the endoluminal stent 100 is described hereinafter. The endoluminal stent 100 may be wrapped around a balloon catheter and may be deployed in a endovascular lumen toward a region where the endoluminal stent 100 is to be placed. Initially, when the balloon catheter travels through the endovascular lumen, the endoluminal stent 100 wrapped around the balloon catheter may be in crimped configuration when. When the balloon catheter reaches to the place inside the endovascular lumen where the endoluminal stent 100 is to be deployed, the balloon may be expanded by blowing a gas into the balloon. As the balloon expands, the outermost ringlets 102 on both the ends of the endoluminal stent 100 may expand resulting in dog boning of the endoluminal stent 100. As a result, longitudinal compressive forces may be induced across the length of the endoluminal stent 100. Now, conventional stents may suffer reduced in the length of the stents resulting in foreshortening. However, the offset connection of the connectors 108 with adjacent ringlets may prevent foreshortening of the endoluminal stent 100. When the longitudinal compressive forces acts on the endoluminal stent 100, the ringlets 102 moves towards each other resulting in the shortening of the endoluminal stent 100. However, as the ringlets 102 moves towards each other, the crowns 104 of the ringlets 102 may abut with the connectors 108 such that the connectors 108 provide extra support to the ringlets to resist the deformation caused due to longitudinal compressive forces. Therefore, when the balloon inflates, the endoluminal stent 100 retains its size thereby preventing foreshortening of the endoluminal stent 100. Further, when the balloon inflates to its maximum volume, the connector 108 may allow the ringlets 102 to retain its structure.

Although implementations for endoluminal stents are described, it is to be understood that the present subject matter is not limited to the specific features or methods described. Rather, the specific features and methods are disclosed as implementations of endoluminal stents.

We claim:

1. An endoluminal stent comprising:
a plurality of ringlets forming a lateral surface of the endoluminal stent, each of the plurality of ringlets having a sinusoidal structure along a length of the ringlet, wherein the sinusoidal structure is formed as contained in a cylindrical plane of the lateral surface of the endoluminal stent, wherein the plurality of ringlets are coaxial to each other and are provided along a central longitudinal axis; and
a plurality of connectors to couple adjacent ringlets, wherein one end of each corresponding connector of the plurality of connectors is coupled to one ringlet at a first junction and another end of the corresponding connector is coupled to an adjacent ringlet at a second junction, wherein an axis passing through the first junction and parallel to the central longitudinal axis is at an offset with respect to another axis passing through the second junction and parallel to the central longitudinal axis, wherein each of the plurality of connectors is of sinusoidal structure and at least one radius in the sinusoidal structure, being measured at a point at least halfway to a midpoint of a corresponding connector, is in a range of 0.4 mm to 0.7 mm, wherein, for each corresponding connector, the first junction is located at a mid-portion of a connecting element that connects ends of two crown peaks that are oriented in opposite directions in the one ringlet and the second junction is located at a mid-portion of another connecting element that connects ends of two crown peaks that are oriented in opposite directions in the adjacent ringlet.

2. The endoluminal stent as claimed in claim 1, wherein each of the plurality of ringlets comprise:
 a plurality of arc-shaped first crowns; and
 a plurality of arc-shaped second crowns, each of the plurality of arc-shaped first crowns and the arc-shaped second crowns having a first end and a second end and an orientation of the plurality of arc-shaped first crowns being opposite to the orientation of the plurality of arc-shaped second crowns.

3. The endoluminal stent as claimed in claim 1, wherein the plurality of ringlets is made of a metal, a metal alloy, a biodegradable polymer, a biostable polymer, and any combination thereof.

4. The endoluminal stent as claimed in claim 1, wherein the plurality of connectors are flexible.

5. The endoluminal stent as claimed in claim 1, wherein material for making ringlets is selected from, but not limited to Stainless steel, Tantalum, Niobium, Magnesium alloys, Zinc alloys, L605, MP25N, Nitinol or a combination of thereof.

6. The endoluminal stent as claimed in claim 1, wherein material for making ringlets is selected from, but not limited to L-lactide, Glycolide or combinations of thereof, poly (hydroxybutyrate), polyorthoesters, poly anhydrides, poly (glycolic acid), poly(glycolide), poly(L-lactic acid), poly(L-lactide), poly(D-lactic acid), poly(D-lactide), poly (caprolactone), poly(trimethylene carbonate), polyester amide, polyesters, polyolefins, polycarbonates, polyoxymethylenes, polyimides, polyethers, and copolymers and combinations thereof.

7. The endoluminal stent as claimed in claim 1, has a coating selected from a biodegradable polymer coating, a biostable polymer coating, a passive coating, a therapeutic agent coating or a combination of thereof.

\* \* \* \* \*